United States Patent [19]

Jackson et al.

[11] Patent Number: 4,748,433

[45] Date of Patent: May 31, 1988

[54] ELECTRO-CONDUCTIVE ELASTOMERIC DEVICES

[75] Inventors: John Jackson, Lesmahagow; Seyed A. Angadjivand, Glasgow, both of Scotland

[73] Assignee: University of Strathclyde, Glasgow, Scotland

[21] Appl. No.: 821,282

[22] Filed: Jan. 22, 1986

[30] Foreign Application Priority Data

Jan. 29, 1985 [GB] United Kingdom ............... 8502197

[51] Int. Cl.$^4$ .............................................. G01B 7/16
[52] U.S. Cl. ........................................ 338/6; 338/47; 338/114
[58] Field of Search ............................... 338/114, 2–6, 338/47, 165, 209, 99

[56] References Cited

U.S. PATENT DOCUMENTS 3,719,913  3/1973  DuBose et al. ............... 338/114 X
4,145,317  3/1979  Sado et al. .................... 338/114 X

*Primary Examiner*—E. A. Goldberg
*Assistant Examiner*—M. M. Lateef
*Attorney, Agent, or Firm*—Bell, Seltzer, Park & Gibson

[57] ABSTRACT

An elastomeric electro-conductive device (10) capable of providing within a predetermined range of elastic elongation ($\lambda$) of the device (10) sensory signals representative of elastic elongation ($\lambda$) imposed on the device includes an elastomeric electro-conductive member (11) bonded to an elastomeric substrate (12). Member (11) and substrate (12) have substantially similar resistance-to-stretch characteristics $\phi$ within the predetermined range. On a Mooney Plot for ($\lambda^{-1}$) values in the range 0.5 to 0.8 $\phi$ is substantially constant at 0.4 M Nm$^{-2}$.

4 Claims, 3 Drawing Sheets

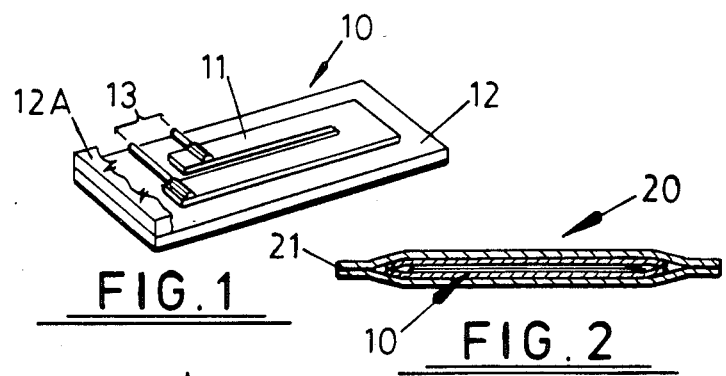
FIG. 1
FIG. 2
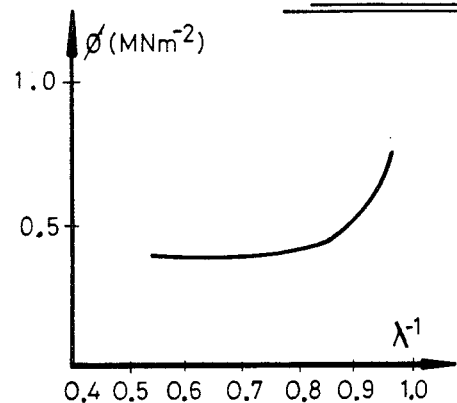
FIG. 3
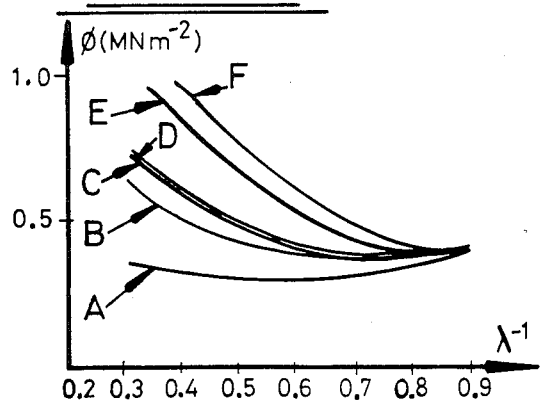
FIG. 4

ELECTRO-CONDUCTIVE ELASTOMERIC DEVICES

FIELD OF THE INVENTION

This invention relates to electro-conductive elastomeric devices, and to methods of production thereof.

BACKGROUND OF THE INVENTION

In our EPC Patent Specification No. 41807 there are disclosed various devices for obtaining a signal which is representative of the mobility of a joint, each of these devices comprising an elastomeric electro-conductive member mounted on an elastomeric substrate and electrically interconnected with a resistance-sensitive electrical network by conductor means. The operation of these devices is such that movement of the joint gives rise to extension and contraction of the elastomeric electro-conductive member as a result of which the electrical resistance of the member varies and this variation is measured by the electrical network. Our EPC Patent Specification No. 89843 discloses various formulations for electro-conductive materials which are suited to use in the devices referred to above.

SUMMARY OF THE INVENTION

It has now been discovered that in such elastomeric electro-conductive devices the relative physical characteristics of the electro-conductive member and of the substrate play an important role in attainment of consistent results and longevity during practical use of the device.

According to the present invention there is provided an elastomeric electro-conductive device for providing within a predetermined range of elastic elongation of the device sensory signals representative of the extent of elastic elongation imposed on the device, said device comprising an elastomeric electro-conductive member mounted on an elastomeric substrate, conductor means being connected to said member for enabling interconnection of the device to an electrical network, wherein the member and the substrate have substantially similar resistance-to-stretch characteristics within said predetermined range.

Preferably said member and said substrate each comprises a silicone polymer gum incorporating fumed silica filler. The quantum of fumed silica filler may differ between the member and the substrate.

Conveniently the member may be made in accordance with any one of the formulations disclosed in the aforesaid EPC Patent Specification No. 89843. Alternatively the base polymer may be C2501 (as manufactured by ICI) for the member and for the substrate. As a further alternative the fixed vegetable oils may be replaced by synthetic oils which are unsaturated and contain carbon chains with 16 carbon atoms or more and also having a similar degree of mesogenicity to unsaturated vegetable oils such as arachis oil. By way of example suitable synthetic oils have two oleic chains, such as di-oleyloxalate which is liquid at room temperature and is characterised by the formula

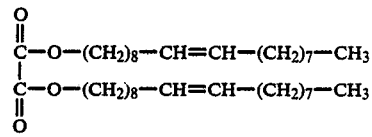

Additionally it is preferred that the materials forming the member are mixed together in the presence of a volatile additive in which the oil and polymer gum dissolve and/or disperse miscibly whereby homogeneity of the material is assured with less dependence upon stringent manufacturing tolerances. Preferred such additives volatilise from the curing mixture of constituents and carry off air, water vapour, and other gaseous substances formed during mixing and/or curing of the mixture and such additives volatilise at approximately the same rate as curing. By way of example such additives may be Toluene, chloroform, tetrahydrofuran, n-Hexane, or SBP3 (sold by ICI Ltd).

Preferably the member and the substrate are in intimate contact over their common areal extent by virtue of an adhesive bonding agent. Conveniently the bonding agent has the same composition as that of the substrate and accordingly has the same resistance-to-stretch characteristics within said predetermined range as both the member and the substrate.

Conveniently the substrate has a higher tear strength than the member.

Preferably each said conductor means is in the form of a length of low-resistance conductive polymer adhesively connected to the member by a bonding material having the same electrical characteristics as the member. By way of example the conductive polymer may be an H.T.V. polymer such as EP494 (made and sold by J-Sil Ltd) and containing about 30% Carbon Black, the polymer being vulcanised at high temperature utilising di-cumyl-peroxide as curing agent. Also, by way of example the bonding material may incorporate the same constituents and in the same proportions as the member whereby the physical and electrical characteristics of the bonding material and said member at identical.

Preferably also said device comprises an elastomeric non-conductive sleeve within which said member and substrate are housed.

Conveniently said sleeve is adhesively bonded to said member and substrate throughout their common areal extent by means of an electrically non-conductive bonding substance such as the bonding agent previously referred to.

Conveniently, said sleeve is made of H.T.V. polymer gum. Preferably also said sleeve has resistance-to-stretch characteristics substantially similar to those of said member and said substrate.

It will be appreciated that the sleeve preferably is possessed of properties which isolate the member and the substrate from the ambient surroundings. By way of example the sleeve may be water-repellant and solvent insensitive. Additionally the sleeve may be hypoallergenic so that the device is relatively safe to be worn next to the skin.

BRIEF DESCRIPTION OF THE DRAWINGS

Embodiments of the present invention will now be described by way of example with reference to the accompanying drawings in which:

FIGS. 1 and 2 schematically illustrate first and second devices in accordance with the present invention;

FIG. 3 illustrates the physical characteristics of the preferred electro-conductive member utilised in the devices of FIGS. 1 and 2;

FIGS. 4, 5 and 6 illustrate the physical characteristics of alternative substrates capable of use in the devices of FIGS. 1 and 2;

DESCRIPTION OF PREFERRED EMBODIMENT

Figure 5:
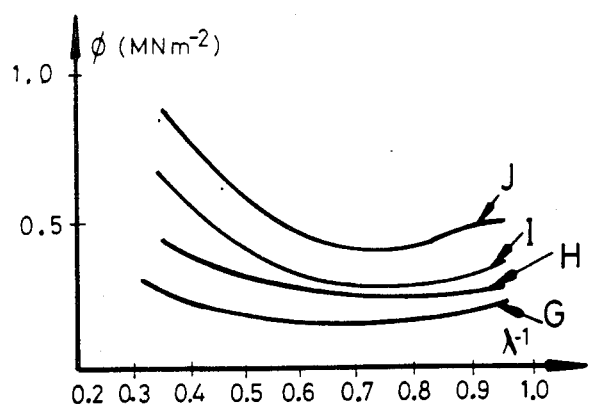

As is shown in FIG. 1 of the drawings, an electro-conductive elastomeric device 10 comprises an elastomeric electro-conductive member 11, in this instance U-shaped, mounted on an elastomeric substrate 12 which is non-conductive. Substrate 12 is a non-conductive R.T.V. silicone polymer and member 11 is a conductive RTV silicone polymer. Conductor means 13 of very low electrical resistance are connected to the free ends of the limbs of the U-shaped member 12 in order to deliver a signal from the device 10 to an electrical network, not shown, which is resistance sensitive. It is preferred that the conductor means 13 take the form of lengths of conductive HTV polymer, such as EP494 loaded with about 30% carbon black, and that the lengths of such polymer are adhesively secured to member 11 by bonding material having the same composition as member 11 so that an intimate electrical connection is formed between conductor means 13 and the member 11 whilst retaining a degree of resiliency at the connection. Furthermore, in order to protect member 11 a second substrate 12A, identical in composition to substrate 12, is arranged to overlie member 11.

FIG. 2 illustrates the device 10 of FIG. 1 forming a sub-assembly for a device 20 comprising device 10 encased in a non-conductive elastomeric sleeve 21. Sleeve 21 preferably has a higher tear strength than does device 10 so that device 20 is of increased robustness.

Member 11 preferably has a composition comprising silicone polymer gum, graphitic carbon particles, crosslinking and curing agents and an unsaturated oil containing carbon chains of 16 carbon atoms or more and having a degree of mesogenicity similar to unsaturated vegetable oils such as archis oil, the relative proportions of these constituents being selected as explained in the aforesaid EPC Patent Specification No. 89843 in order to achieve the desired physical and electrical properties. By way of example the preferred formulation is 100 g silicone polymer gum (C2501—supplied by J-Sil Ltd.), 70 g graphitic carbon (having a particle size of the order of 50 microns), 20 g arachis oil, 2 g DBTL (Di-butyl-timdilaurate) as curing agent, and 5 g of Silester O.S. as crosslinking agent, these constituents having been mixed together in the presence of 100 ml of toluene which is a volatile additive functioning to dissolve and/or disperse the graphitic carbon within the mixture.

The physical characteristics of the exemplified formulation of member 11 are depicted in FIG. 3 which is a Mooney Plot of $F/A(\lambda-\lambda^{-2})$ against $\lambda^{-1}$ where F is the force, A=cross-sectional area, and elongation $\lambda=l/l_o$ where l and $l_o$ are the lengths of a tested sample in the deformed and undeformed states respectively. It will be appreciated that a Mooney Plot is a well known technique for representing the physical characteristics of an elastomeric material and the ordinate (Y-axis) denotes the function $\phi$ where $$\phi = \frac{\text{Force }(F)}{\text{Area of }X\text{-Sec }(A) \times (\lambda - \lambda^{-2})}$$

whilst the abscissa (X-axis) denotes the function $\lambda^{-1}$. When the slope of the Mooney Plot is paralle to the X-axis there is no hysteresis. $\phi$ is representative of resistance to extension (i.e. stretch).

It will be seen from FIG. 3 that for the exemplified member 11, $\phi$ has a value of the order of 0.4M Nm$^{-2}$ over the range of $\lambda^{-1}$ vaues of 0.5 to 0.8. In accordance with the present invention substrate 12 is arranged to have substantially similar $\phi$ values over the same range of $\lambda^{-1}$.

By way of example, substrate 12 may be an RTV polymer comprising the same polymer gum as is utilised in member 11 and mixed with the same cross-linking and curing agents but without incorporating the graphitic carbon or the oil constituents of member 11. In particular FIG. 4 shows Mooney Plots of various formulations of substrate 12 with various relative proportions of polymer gum C2501 and polymer gum C (as sold by ICI Ltd. under product code number 11635) from which it will be appreciated that the $\phi$ characteristic can be varied in a predetermined manner by selecting the relative proportions of the two gums.

In FIG. 4, graph A is for 50 g Polymer C and zero C2501 gum, graph B is for 37.5 g Polymer C and 12.5 g C2501 gum, graph C is for 30 g Polymer C and 20 g C2501 gum, graph D is for 25 g Polymer C and 25 g C2501 gum, graph E is for 12.5 g Polymer C and 37.5 g C2501 gum, and graph F is for zero Polymer C and 50 g C2501 gum. In each case there is therefore 50 g Polymer gum which is crosslinked with a fixed amount of Crosslinker and cured with a fixed amount of curing agent.

Similarly various relative proportions of polymer gum C2501 and polymer gum B (as sold by ICI Ltd. under product code number 11636) result in a somewhat similar set of Mooney Plots so that by mixing gum C2501 with either gum B or gum C or with both gums B and C a large family of $\phi$ characteristics can be achieved. In this connection gum C2501 is itself silica filled polymer C with a viscosity of the order of 400 centipoises and the effect of adding either or both of polymers B and C is to render the mixture less viscous. Polymer B gum has a higher molecular weight than polymer C gum and is preferred to polymer C gum because it reduces hysteresis in the resultant materials, i.e. the $\phi$ characteristics are somewhat flatter over the range of $\lambda^{-1}$ of interest.

FIG. 5 illustrates the effect of varying the amount of crosslinking agent in the substrate 12 when the polymer gum mixture is held constant at equal proportions of C2501 and polymer C gum in the presence of a constant 1% by weight amount of curing agent and it can be seen that a further family of $\phi$ curves results. Increased amounts of the crosslinker lead to increased crosslinked density with increased tensile strength and reduced elongation at break in the sampled material. Curve G is for 1% by weight of crosslinker, curve H is for 3% by weight crosslinker, curve I is for 5% by weight of crosslinker and curve J is for 7% by weight crosslinker.

Figure 6:
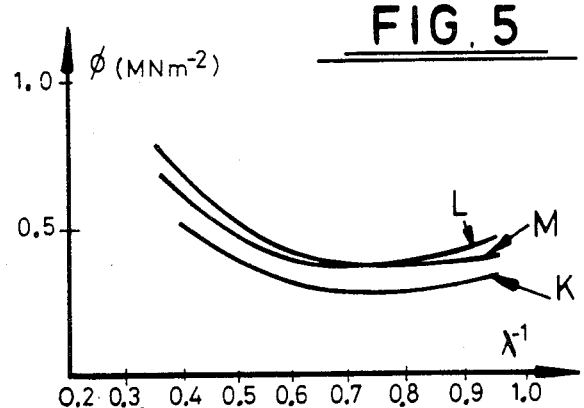

FIG. 6 illustrates comparable results in the substrate 12 for varying amounts of curing agent in the test polymer mix of equal parts C2501 and gum C in the presence of a constant 5% by weight of crosslinker. Curve K is for 2% by weight of curing agent, curve L is for 1% by weight of curing agent, and curve M is for 0.5% by weight of curing agent.

Figure 7:
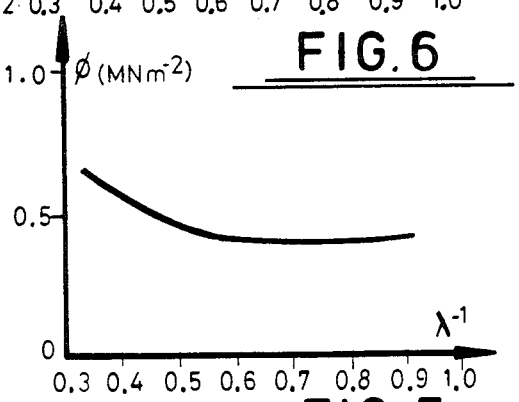
FIG. 7 illustrates the physical characteristics of the preferred substrate utilised in the devices of FIGS. 1 and 2.

It will be appreciated from the results shown in FIGS. 4, 5 and 6 that by selecting the mixture of polymer gums and the proportions of crosslinking and curing agents the substrate 12 can be arranged to have resistance-to-stretch characteristics of a predetermined nature within a fairly wide bandwidth. In particular, FIG. 7 illustrates the preferred characteristics of the substrate 12 for compatibility with the characteristics of the preferred electro-conductive member 11 (as shown in FIG. 3), i.e. within the $\lambda^{-1}$ range of 0.5 to 0.8 $\phi$ is substantially constant at about 0.4M $Nm^{-2}$, these substrate characteristics being obtained from a formulation of 50 g C2501, 50 g gum C, 5 g crosslinking agent (Silester O.S.), 2 g curing agent (DBTL).

In order to fabricate the device 10 of FIG. 1, member 11 is adhesively bonded to substrate 12 by lightly coating the undersurface of member 11 with a bonding agent and it is preferred that the bonding agent has the same composition as the substrate 12, it being understood that this composition vulcanises at room temperature and is capable of functioning as an adhesive during its curing phase. Following vulcanisation of the bonding agent the conductor means 13 are attached as previously explained, then a further substrate 12A identical to substrate 12 is adhesively bonded to overlie the combination of elements 11, 12 and 13, by means of the same bonding agent (i.e. having the same composition as substrate 12).

With regard to the device 20 of FIG. 2 sleeve 21 in one example is formed of upper and lower pieces of HTV polymer material bonded with a non-conductive RTV bonding substance identical to the bonding agent referred to (i.e. having the same composition as substrate 12), the bonding substance being disposed so as completely to exclude air from the interior of the device. Also, the sleeve 21 is arranged to have substantially similar resistance-to-stretch characteristics as the member 11 within the working range, that is, within the appropriate range of $\lambda^{-1}$, the $\phi$ value of the sleeve material has the same shape as that of the member 11; preferably the two $\phi$ values are approximately equal in magnitude.

Figure 8:
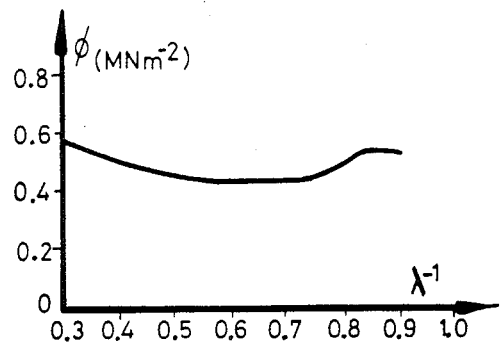
FIG. 8 illustrates the physical characteristics of the preferred sleeve utilised in the device of FIG. 2.

By way of example, the sleeve 21 may have a formulation comprising silicone polymer gum E368 (supplied by J-Sil Ltd.) which is a methyl-vinyl-polysiloxane containing a small percentage of fumed silica filler. This gum is vulcanised at high temperature by 2,4 di-chlorobenzoyl peroxide acting as curing agent and is post cured at a moderate temperature for a duration of some hours. The resultant material has a Mooney Plot as shown in FIG. 8 from which it will be seen that within the $\lambda^{-1}$ range of 0.5 to 0.8 $\phi$ has a value within the range 0.5 to 0.4M $Nm^{-2}$.

Figure 9:
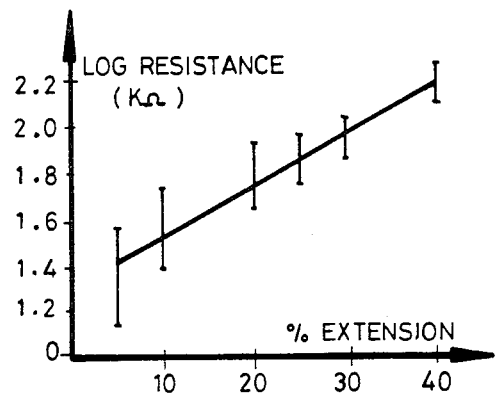
FIG. 9 illustrates the electrical resistance/extension characteristics of a FIG. 2 device.

By way of example in the device 10 of FIG. 1 substrate 12 may have dimensions of 135 mm by 35 mm × 0.3 mm whilst member 11 may have an overall length of 130 mm, a total width of 16 mm, and a thickness of 0.3 mm, each limb of the U-shape being 7 mm in width and the base portion of the U-shape being 8 mm in width, one limb being 7 mm shorter than the other limb so that the two conductors 13 can both emerge at the same side of the device. When such a device 10 is incorporated into device 20 of FIG. 2 each of the upper and lower portions of the sleeve 21 has a length of 400 mm, a width of 38 mm, and a thickness of 0.4 mm. In each case the formulation of the materials is as previously exemplified, and as regards this embodiment of the device 20 the electrical resistance/extension characteristic is as shown in FIG. 9 in which the vertical lines represent the standard deviation range of the resistance at particular extensions arising from the testing of numerous samples of the material.

It will be appreciated that the devices 10, 20 referred to above with dimensional details are intended to be used with longitudinal extension forces applied thereto and in this mode of operation the relative thickness of the member 11, the substrate(s) 12, 12A, and the sleeve 21 (if present) can be adjusted in order to match the stress/strain plot to the specific application in which the device is to be used.

Furthermore as regards such devices 10, 20, as are intended to be used with lateral compressive forces applied thereto it is preferable that the member 11 is supported by a relatively thick substrate 12 (seated against an inelastic base), the member 11 being surfaced by a relatively thin substrate 12A (but having substantially the same composition as substrate 12). By way of example the thick substrate 12 may have a thickness of about 100 mm and a formulation of 100 g polymer gum A (as manufactured by ICI Ltd under their product code 11637), 3 g Silester O.S. acting as crosslinking agent, and 1 g of 3, amino propyltriethoxysilane acting as curing agent. The thin substrate 12A referred to in this case may have a thickness of 0.3 mm and a formulation of 100 g C2501 polymer gum, 5 g Silester O.S. acting as crosslinking agent, and 2 g DBTL acting as curing agent.

What is claimed is:

1. An elastomeric electro-conductive strain gauge device for providing within a predetermined range of elastic elongation of the device sensory signals representative of the extent of elastic elongation imposed on the device, said device comprising an elastomeric substrate, an elastomeric electro-conductive member mounted on said elastomeric substrate, conductor means being connected to said member for enabling interconnection of said device to an electrical network, wherein said member and said substrate comprise substantially similar resistance-to-stretch characteristics within said predetermined range of elastic elongation, and wherein, within said predetermined range of elastic elongation, the resistance-to-stretch characteristic $\phi$ of said member and of said substrate is substantially constant and equal in value.

2. A device as claimed in claim 1, wherein said predetermined range of elastic elongation is 25% to 100% elongation.

3. A device as claimed in claim 2, wherein the resistance-to-stretch characteristic $\phi$ has a Mooney Plot value of 0.4M $Nm^{-2}$.

4. An elastomeric electro-conductive strain gauge device for providing within a predetermined range of elastic elongation of the device sensory signals representative of the extent of elastic elongation imposed on the device, said device comprising an elastomeric substrate, an elastomeric electro-conductive member mounted on said elastomeric substrate, conductor means being connected to said member for enabling interconnection of said device to an electrical network, wherein said member and said substrate comprise substantially similar resistance-to-stretch characteristics within said predetermined range of elastic elongation, and wherein said device further comprises an elastomeric non-conductive sleeve encasing said member, substrate and conductor means, said sleeve having resistance-to-stretch characteristics $\phi$ substantially similar to those of said member and substrate within said predetermined range of elastic elongation and the resistance-to-stretch characteristic $\phi$ of said sleeve has a Mooney Plot value in the range $0.4M\ Nm^{-2}$ to $0.5M\ Nm^{-2}$ within the elastic elongation range 25% to 100% elongation.

* * * * *